United States Patent [19]

Hitzman

[11] 4,414,334

[45] Nov. 8, 1983

[54] OXYGEN SCAVENGING WITH ENZYMES

[75] Inventor: Donald O. Hitzman, Bartlesville, Okla.

[73] Assignee: Phillips Petroleum Company, Bartlesville, Okla.

[21] Appl. No.: 291,146

[22] Filed: Aug. 7, 1981

[51] Int. Cl.³ .............. C12N 9/04; C10G 32/00; C12R 1/84

[52] U.S. Cl. .............. 435/262; 426/7; 426/12; 435/190; 435/281; 435/938

[58] Field of Search .............. 435/190, 262, 264, 247, 435/938, 281; 426/7, 10, 8, 34, 12

[56] References Cited

U.S. PATENT DOCUMENTS

| | | | |
|---|---|---|---|
| Re. 23,523 | 7/1952 | Baker | 99/48 |
| 2,752,221 | 6/1956 | Wachter et al. | 21/2.5 |
| 2,758,932 | 8/1956 | Scott | 426/8 |
| 2,801,697 | 8/1957 | Rohrback | 166/1 |
| 2,940,904 | 6/1960 | Ohlmeyer | 435/190 |
| 2,971,850 | 2/1961 | Barton | 426/61 |
| 2,971,851 | 2/1961 | Kurtz | 426/61 |
| 3,005,714 | 10/1961 | Cooper | 99/54 |
| 3,016,336 | 1/1962 | Scott et al. | 195/63 |
| 3,019,195 | 1/1962 | Denman et al. | 252/389 |
| 3,036,305 | 5/1962 | Channabasappi et al. | 21/2.7 |
| 3,065,193 | 11/1962 | Volk | 260/29.6 |
| 3,095,307 | 6/1963 | Scott et al. | 99/171 |
| 3,150,086 | 9/1964 | Marsh et al. | 252/8.55 |
| 3,160,508 | 12/1964 | Scott | 435/190 X |
| 3,163,619 | 12/1964 | Sheafs et al. | 260/29.6 |
| 3,193,393 | 7/1965 | Scott | 435/190 X |
| 3,234,163 | 2/1966 | Schurz et al. | 260/29.6 |
| 3,235,523 | 2/1966 | Schurz et al. | 260/29.6 |
| 3,326,286 | 6/1967 | Harvey | 166/9 |
| 3,340,930 | 9/1967 | Hitzman | 166/9 |
| 3,343,601 | 9/1967 | Pye | 166/42 |
| 3,372,749 | 3/1968 | Williams | 166/9 |
| 3,399,725 | 9/1968 | Pye | 166/9 |
| 3,505,244 | 4/1970 | Cessna | 252/391 |
| 3,532,166 | 10/1970 | Williams | 166/274 |
| 3,598,181 | 8/1971 | Wegner et al. | 166/246 |
| 3,650,326 | 3/1972 | Hitzman | 166/246 |
| 3,747,676 | 7/1973 | Norton | 166/275 |
| 3,770,055 | 11/1973 | Larsen | 166/244 C |
| 3,800,877 | 4/1974 | Knight | 166/305 R |
| 3,974,066 | 8/1976 | Brown et al. | 208/289 |
| 4,033,896 | 7/1977 | Mitchell et al. | 252/389 |
| 4,042,772 | 8/1977 | Ballweber et al. | 526/220 |
| 4,059,533 | 11/1977 | Watson et al. | 252/8.5 |
| 4,089,789 | 5/1978 | Muzyczko et al. | 252/8.55 E |
| 4,096,073 | 6/1978 | Hitzman | 252/8.55 D |
| 4,124,073 | 11/1978 | Wier | 166/272 |
| 4,128,482 | 12/1978 | Knight | 252/8.55 D |
| 4,248,969 | 2/1981 | Lee | 435/176 |
| 4,250,261 | 2/1981 | Eggeling et al. | 435/190 |
| 4,266,034 | 5/1981 | Patel | 435/253 |

OTHER PUBLICATIONS

Kato et al., Enzyme System For Methanol Oxidation in Yeasts, Agr. Biol. Chem., vol. 38, No. 3, 1974, (pp. 675-677).

Simisker et al., Enzymes Participating in the Oxidation of Methanol in Methanol-Assimilating Yeasts, Chem. Abstr., vol. 89: 103375t, 1978.

Chem. Abstracts 90:119744u; 69:51067; 86:28500n.

Drilling Specialties Co., "Multi-Purpose Mud Conditioner", Bulletin 230.

Phillips Chemical Co., "Biochemical Technical Information Alcohol Oxidase", (Brochure Released about Jun. 15, 1981).

Aibz et al., Immobilized Enzymes, Biochemical Engineering, 2nd Ed., Academic Press, Inc. 1973, (pp. 393-396 and 407-417).

Baratti et al., Preparation and Properties of Immobilized Methanol Oxidase, Biotech. and Bioeng. vol. XX, No. 3, 1978, (pp. 333-348).

*Primary Examiner*—David M. Naff

[57] ABSTRACT

Removal of ambient oxygen from aqueous liquids is effectively catalyzed by enzymatic deoxygenation systems comprising alcohol oxidase in the presence of alcohol optionally with catalase. Suitable deoxygenation systems described can be used to alleviate corrosion and oxidative degradation in areas such as oil field fluids, circulating water systems, water storage tanks, alcoholic beverages and foodstuffs. As desired, the enzymatic systems can be immobilized on supports or used in solution.

17 Claims, 3 Drawing Figures

DETERMINATION OF OPTIMUM ALCOHOL OXIDASE CONCENTRATION
IN OXIDASE-METHANOL SCAVENGING SYSTEM.

OXYGEN SCAVENGING WITH ENZYMES

FIELD OF THE INVENTION

The invention relates to compositions and methods to reduce the concentration of oxygen in aqueous liquids.

BACKGROUND OF THE INVENTION

Many materials deteriorate in the presence of oxygen and water. Such materials typically include various metals such as iron, which corrodes in contact with water and oxygen such as in cooling water, drilling muds, and the like; but also include many materials of organic nature used industrially or in foods.

Partially hydrolyzed polyacrylamides and copolymers of acrylamide and acrylic acid, and the alkali salts thereof, are polymeric viscosifiers useful as mobility reducing agents in secondary and tertiary oil recovery processes. However, oxygen usually present in the thickened aqueous fluids containing such viscosifiers tends to degrade the polymer resulting in loss of solution viscosity.

Various methods have been used to avoid the deteriorative effects of oxygen on structural materials in contact with water, including various coatings, corrosion inhibitors, reducing agents to react with the oxygen, stabilizers, and the like. However, all have shortcomings in regard to toxicity, reactivity, cost, and/or lack of long term effectiveness.

Canned food and beverage products, such as wines, beer, ciders, and other closed-container-stored foods, can deteriorate even in the container when oxygen is co-present, as evidenced by changes in color, odor, taste, flavor, or vitamin content, or can rusting. The oxidative degradation also can occur after the container is opened. Canned fruit juices such as apple cider, orange juice, and the like, are adversely affected by oxygen. Other products such as canned vegetables and canned milk can also suffer detrimental effects.

Degradation of foods or degradation of polymeric viscosifiers in oil field fluids due to oxygen is a problem which has engendered numerous solutions.

The oil field fluid for example, can be drilling fluids or muds used in drilling wells. Such drilling fluids include, for example, weighted muds, unweighted muds, and salt water muds, and further can comprise additives frequently added to these muds such as carboxyalkyl ethers such as carboxymethylcellulose and the like, polyglycosans, polyacrylamides, and the like. These latter additives frequently are susceptible to oxidative degradation in the presence of free oxygen. In addition, the drilling fluids usually are handled by equipment susceptible to oxidative degradation as a result of the presence of free oxygen in the aqueous drilling fluid.

The term oil field fluid further includes such as workover fluids, which are aqueous fluids used after the well casing is set and usually, but not necessarily, after primary or self-pressurized recovery of hydrocarbon is terminated. As thus used, workover fluids include such fluids as water or brine floods used in secondary recovery as well as caustic flooding, steam, surfactant flooding and the like used in tertiary recovery. The term also includes mobility buffer fluids such as viscosified or thickened water wherein the water is viscosified or thickened by the addition of such as, for example, polyacrylamide, carboxyalkyl cellulose ethers, biopolysaccharides, and the like. Carbon dioxide which can be pumped into formations to reduce the viscosity of the hydrocarbon in situ for enhanced oil recovery can be present.

Frequently the presence of oxygen in these fluids is deleterious to one or more components of the fluid, i.e., one or more components of the fluid is susceptible to oxidative degradation or the presence of oxygen can be otherwise deleterious.

Thus, for example, polyacrylamides are known to degrade to smaller molecular fragments in the presence of free oxygen. Similarly, carboxyalkyl ethers of cellulose and polyglycosans or biopolysaccharides can be adversely affected by the presence of oxygen either directly or as mediated by aerobic microorganisms. Further small amounts of oxygen present in such as carbon dioxide used in enhanced oil recovery can greatly reduce solubility of the $CO_2$ in the hydrocarbon in situ and thereby reduce the effectiveness of the $CO_2$ for enhanced oil recovery.

In addition to these deleterious effects of oxygen on components of or the effectiveness of oil field fluids themselves, the presence of oxygen can be highly deleterious to the equipments used in handling such fluids such as, for example, pumps, conduits, well casings and the like.

The fluid comprising water and oxygen to be treated can be recycle water such as cooling water, and the like. The presence of free oxygen in such fluids can contribute significantly to the corrosion of associated equipments such as reservoirs, pumps conduits and the like.

New solutions to old problems are desirable, especially new ways which offer a significant advantage or improvement over previous methods.

SUMMARY OF THE INVENTION

I have discovered an effective method of reducing the amount of oxygen present in an aqueous fluid, and thus protecting materials otherwise susceptible to oxidative degradation in the presence of free (dissolved) oxygen. My method comprises reacting the oxygen with an alcohol selected from the group consisting of methanol, ethanol, propanol, and butanol, in the further presence of alcohol oxidase. An oxygen containing aqueous fluid, as I use the phrase, is a fluid comprising water and free oxygen. The fluid containing free oxygen can be such as, for example, oil field fluids, recycle water, foodstuffs, and the like.

My method is particularly applicable to oil field aqueous fluid systems to protect oil field equipment, and to avoid molecular degradation of polymeric viscosifiers used in floods, and the like; and in the treatment of foodstuffs.

By my method, the removal of dissolved oxygen from aqueous liquids is effectively catalyzed by enzymatic deoxygenation systems comprising alcohol oxidase in the presence of alcohol optionally with catalase. Suitable deoxygenation systems described herein are effective to alleviate corrosion and oxidative degradation in such as oil field fluids such as mobility buffers and drillings muds, circulating water systems, water storage tanks, alcoholic beverages and other foodstuffs, and the like. The enzymatic systems can be immobilized on supports or used in solution.

Enzymatic catalysis of oxygen removal is illustrated by the equations:

$$2ROH + 2O_2 \xrightarrow{\text{Alcohol Oxidase}} 2R'CHO + 2H_2O_2 \quad \text{(A)}$$

-continued

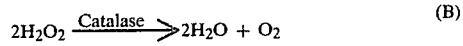

$$2H_2O_2 \xrightarrow{\text{Catalase}} 2H_2O + O_2 \qquad (B)$$

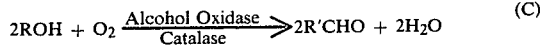

$$2ROH + O_2 \xrightarrow[\text{Catalase}]{\text{Alcohol Oxidase}} 2R'CHO + 2H_2O \qquad (C)$$

wherein R is an alkyl group containing 1 to 4 carbon atoms and R' is hydrogen or an alkyl group containing 1 to 3 carbon atoms.

The enzyme catalase is contained in alcohol oxidase preparations derived from single cell protein production, except in very high purity alcohol oxidase preparations refined by dialysis. The above equations (A), (B), and (C) together illustrate the minimization of both oxygen and by-product hydrogen peroxide by applying an alcohol oxidase/catalase combination to an oxygen-contaminated aqueous alcohol system.

High purity alcohol oxidase, without need for catalase, is applicable in situations wherein oxygen is undesirable but by-product aldehyde and hydrogen peroxide (from alcohol oxidase), are not detrimental. For example, in a system comprising methanol the by-products are formaldehyde and $H_2O_2$:

$$CH_3OH + O_2 \xrightarrow{\text{Methanol Oxidase}} HCHO + H_2O_2 \qquad (D)$$

The alcohol oxidase and catalase enzymes catalyze the removal of oxygen in the presence, e.g., of methanol or ethanol, with the final products being, respectively, formaldehyde or acetaldehyde, and water.

As a catalyst, the enzyme is not consumed but functions continuously as long as oxygen and aqueous alcohol are both present. It is noteworthy that reaction ceases if ambient oxygen is depleted but is resumed if more oxygen is introduced into the system. Therefore, additional oxygen is continuously removed and the enzymes, unlike conventional oxygen scavengers, are not used up. Thus only a relatively small amount of enzyme is required to catalyze the removal of a relatively large amount of oxygen from aqueous alcohol mixtures.

The enzymes in (1) whole cell suspensions and (2) ruptured cell homogenates from single cell protein production are applicable to alleviate corrosion in areas wherein plugging is no problem such as in drilling muds. The enzymes contained in (3) cell-free supernatants or even (4) the purified alcohol oxidase enzyme are preferred for oxygen removal in applications wherein plugging of apparatus and/or subterranean formations, e.g., is undesirable. All four of the above-mentioned enzyme preparations are obtainable from single cell protein production and useful in the broad sense for catalysis of oxygen removal in aqueous fluids.

In applications where $H_2O_2$ by-product is undesirable, e.g., in thickened aqueous waterfloods, the enzyme-containing system requires both alcohol oxidase and catalase. Thus, whole cell suspensions, ruptured cell homogenates and cell-free supernatants are most useful. The cell-free supernatants are preferred in water distribution systems such as closed cooling water systems and for polymer floods in tight subterranean formations. Where desired in some instances, the enzymes can be immobilized on a support such as alumina so that the enzymes do not actually enter the water but catalyze oxygen removal as the water containing dissolved oxygen and alcohol passes through or over the enzymes.

In applications where the $H_2O_2$ by-product is preferred such as in selected drilling muds, the purified alcohol oxidase is used. The generated $H_2O_2$, e.g., can react with the carboxymethylcellulose or starch in drilling muds to improve the product. Another use of the purified alcohol oxidase is in waterfloods wherein the by-product $H_2O_2$ functions as a biocide against downhole anaerobic microorganisms. In such applications a dual biocidal effect would be produced from the alcohol added, e.g., $CH_3OH$, and the by-product $H_2O_2$ generated in-situ. The further injection of $O_2$ downhole to produce more $H_2O_2$ in-situ would provide additional biocidal effects.

For use in alcoholic beverages and foodstuffs, each application must be considered individually since, e.g., the effects of by-product $H_2O_2$ and aldehydes may or may not be detrimental, which would dictate the preferred enzyme-containing system.

ALLEVIATION OF CORROSION IN WATER DISTRIBUTION SYSTEMS

Since one of the principal corrosive components in cooling water systems is dissolved oxygen, the present invention has application in deceasing metal corrosion by maintaining the dissolved oxygen of the cooling water at a low concentration.

In addition to dissolved oxygen, other corrosive ingredients in water systems include inorganic salts such as the carbonates, bicarbonates, chlorides, and sulfates of such as sodium, magnesium, and calcium. Brines, containing dissolved oxygen are recognized as being more corrosive than fresh water. Corrosion rates are known to be promoted by temperature increases, and by reductions in pH. In cooling water systems in general, the concentrations of inorganic salts or ions frequently are significantly higher than in ordinary tap water.

Thus, the inventive deoxygenation systems are useful in decreasing or preventing the corrosion of corrosion-susceptible metals, particularly iron, which are in contact with closed circulating oxygen-containing water systems such as those passing through condensers, engine jackets, heat exchangers, evaporators, distribution systems, and the like as well as water storage tanks. The oxygen-scavenging systems thus help to avoid corrosion of metals commonly used in circulating water systems particularly ferrous metals including iron and steel, and also galvanized steel as well as non-ferrous metals including copper and its alloys, aluminum and its alloys, and brass. Of course, on a practical basis, it is not feasible to deoxygenate a cooling tower or evaporative condenser water due to constant re-saturation with air (oxygen).

ALLEVIATION OF OXIDATIVE DEGRADATION IN FOODSTUFFS

The detrimental effects of oxidative degradation in foods, solid or liquid, develop rapidly as evidenced, e.g., by changes in flavor, color and destruction of vitamin content. In some foods these reactions occur very rapidly and sometimes even before processing is completed. Another aspect of the problem is the materials of construction used in the food containers themselves such as metals susceptible to corrosion promoted by the presence of oxygen. Canned fruit juices such as apple cider, orange juice, and the like are adversely affected by ambient oxygen. Other products such as canned vegetables and canned milk also suffer detrimental effects such as souring and discoloration in the presence of ambient oxygen.

The enzymatic-catalyzed deoxygenation systems of the present teaching can effectively eliminate the ambient oxygen in packaged foodstuffs and thereby alleviate the detrimental effects of oxidative degradation discussed above.

BRIEF DESCRIPTION OF THE FIGURES

FIGS. 2 and 3 illustrate the effectiveness of alcohol oxidase/methanol systems in removing oxygen from an oxygen-saturated tap water.

DETAILED DESCRIPTION OF THE INVENTION

Figure 1:
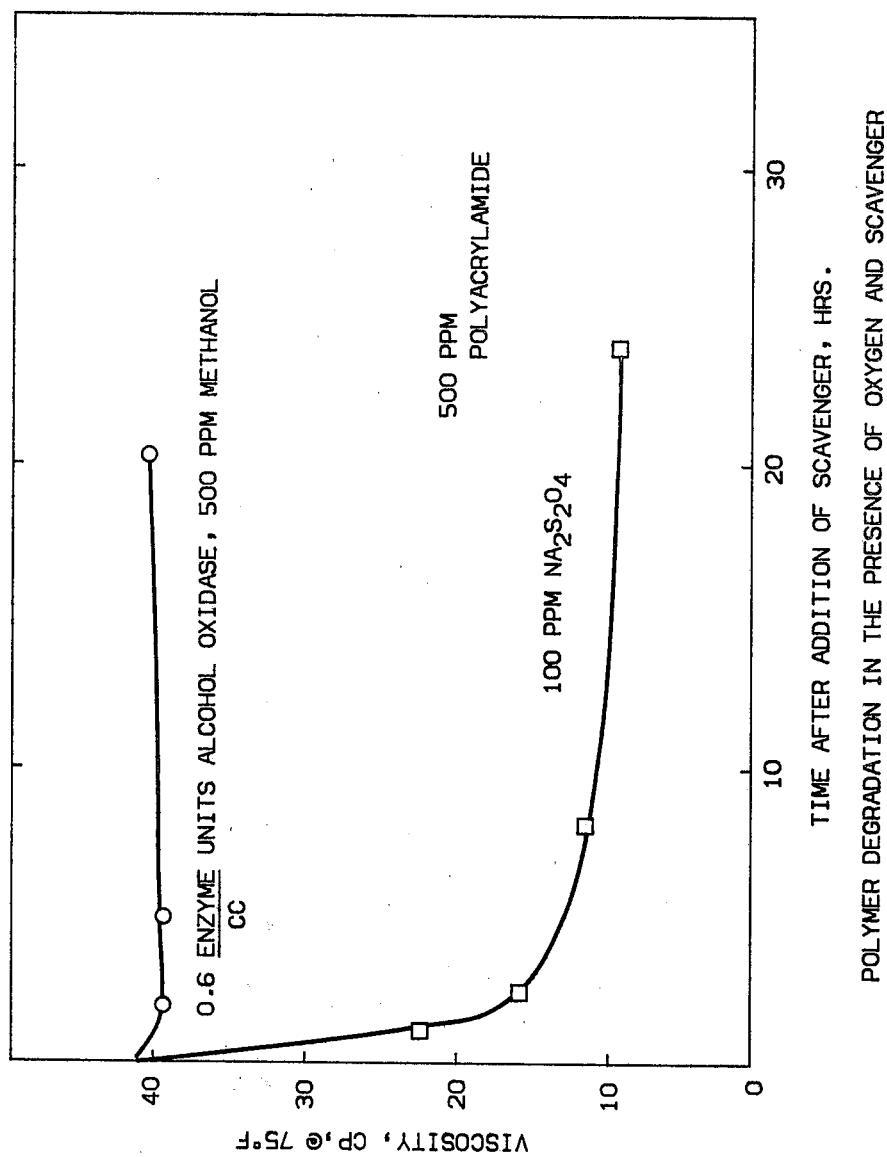
FIGS. 1, 2, and 3 attached are discussed in more detail in the context of the Examples. Briefly, FIG. 1 compares viscosities with time of dilute aqueous polyacrylamide solutions containing respectively alcohol oxidase and sodium hydrosulfite, showing much higher effectiveness of the oxidase in protecting the polymer from oxygen degradation.

According to my invention an aqueous liquid containing free oxygen is treated with alcohol oxidase and an alcohol selected from $C_1$ to $C_4$ straight chain alkanols to thereby reduce or eliminate the dissolved oxygen. Alcohol oxidase is isolatable from various microorganisms capable of growth on lower chain alkanols. The alcohol oxidase catalyzes the following reaction:

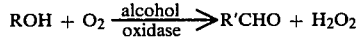

$$ROH + O_2 \xrightarrow{\text{alcohol oxidase}} R'CHO + H_2O_2$$

wherein R is an alkyl group having from 1 to 4 carbon atoms and R' is hydrogen or an alkyl group having one less carbon atom than R.

Suitable microorganisms which can be cultured on an aqueous methanol-containing substrate and thus provide a source of alcohol oxidase include the following: *Gliocladium deliquescens, Paecilomyces varioti, Trichoderma lignorum, Candida boidinii, Candida methanolica, Candida parapsilosis, Hansenula capsulata, Hansenula glycozyma, Hansenula henricii, Hansenula minuta, Hansenula nonfermentans, Hansenula philodendra, Hansenula polymorpha, Hansenula wickerhamii, Kloeckera species, Pichia haplophila, Pichia lindnerii, Pichia pastoris, Pichia pinus, Pichia trehalophila, Torulopsis glabrata, Torulopsis pinus, Torulopsis methandomerquiii, Torulopsis methanolovescens, Torulopsis methanosorbosa, Torulopsis nitratophila* and the like. The particularly preferred alcohol oxidases are recovered from cells of *Hansenula polymorpha* and *Pichia pastoris*.

The presently preferred alcohol oxidase is obtained from methanol utilizing Pichia-type microorganisms comprising microorganisms of genus Pichia and microorganisms genetically and/or taxonomically closely related to Pichia. Specific examples of such methanol-utilizing Pichia yeast include: *Pichia pastoris, Pichia pinus, Pichia trehalophila,* and *Pichia molischiana.*

Alcohol oxidase can be obtained commercially from chemical and biological supply houses. However, in a preferred embodiment the alcohol oxidase is obtained from fermentation of an alcohol by a selected microorganism followed by separation of the alcohol oxidase.

An alcohol oxidase (alcohol: oxygen oxidoreductase) is isolated from *Pichia pastoris* in soluble form, or crystallized to purity, using a dialysis precipitation procedure. This yeast contains about 20 percent of its total protein as alcohol oxidase. The enzyme was isolated from a suspension of cells taken from a fermenter by homogenizing in a Dynomill glass-bead mill and separating the resultant supernatant containing the alcohol oxidase from the cellular debris by centrifugation. This supernatant, which contains 200–300 enzyme units (Eu) per mL, can be further treated by adjusting the pH to 6.5 and dialyzing against 10 volumes of water. When the molar ionic strength of the crude enzyme solution decreases to about 0.02 M sodium phosphate, a precipitate of the alcohol oxidase forms. The precipitate contains over 80 percent of the enzyme units present in the supernatant and is approximately 95 percent pure alcohol oxidase.

The above supernatant with relatively high enzymatic activity (200–300 Eu/mL) also contains large amounts of catalase, an enzyme which rapidly dismutates two moles of hydrogen peroxides into one mole of oxygen gas and two moles of water. Thus, alcohol oxidase is obtainable from *Pichia pastoris* in various degrees of purity:

(a) Whole single cell protein suspension: Both alcohol oxidase and catalase enzymes are available over long time periods by diffusion through cell walls.

(b) Homogenate of ruptured cells: Both alcohol oxidase and catalase enzymes are available in solution with significant amounts of cellular debris.

(c) Supernatant after centrifugation of (b): The cell-free supernatant contains relatively high enzymatic activity (200–300 Eu/mL) comprising alcohol oxidase and catalase.

(d) High purity alcohol oxidase by dialysis of (c): The precipitated alcohol oxidase of about 95% purity accounts for over 80% of the enzymatic activity of the above supernatant.

Copending application Serial No. 45,715 filed June 5, 1979, now abandoned, discloses the catalytic alcohol oxidase deoxygenation system. I hereby incorporate by reference said application and all of its descriptive disclosure herein in total.

Broadly, according to a preferred method of preparing the alcohol oxidase, an aqueous suspension of cells having alcohol oxidase activity is prepared by fermentation of methanol as carbon energy substrate using a methanol-utilizing microorganism. This aqueous suspension of cells, hereinafter referred to as "alcohol oxidase preparation I" or "AOPI", exhibits alcohol oxidase activity over a relatively long period of time by diffusion thereof through the cell walls.

The aqueous suspension of cells can be homogenized to produce a homogenate, referred to as "alcohol oxidase preparation II" or "AOPII", having alcohol oxidase activity.

Suspended solids can be removed from such a homogenate by centrifugation, filtration, or the like, and the resulting supernatant or cell-free fluid can be used as a crude solution, referred to as "alcohol oxidase preparation III" or "AOPIII", having alcohol oxidase activity.

A crystalline, electrophoretically pure alcohol oxidase, referred to as "alcohol oxidase preparation IV" or "AOPIV", can be further prepared from AOPIII by ultrafiltration or dialysis or by other suitable means, presently preferably and conveniently by dialysis.

In a number of applications wherein $H_2O_2$ by-product is undesirable, it is desirable that the enzyme catalase also be present in the enzyme treatment of aqueous fluids which contain deleterious amounts of free oxygen.

The net effect of the reactions catalyzed by the enzyme combination of alcohol oxidase and catalase is the effective scavenging of free oxygen and the conversion of the by-product $H_2O_2$ into water.

Alcohol oxidase preparations AOPI, AOPII, and AOPIII each have substantial catalase activity so that additional catalase need not be added when combined alcohol oxidase and catalase activity in accordance with the invention is required.

Crystalline alcohol oxidase, AOPIV, however, is substantially free of catalase activity and is the preferred preparation where the presence of $H_2O_2$ is not undesirable. Alternatively, of course, catalase can be added to the AOPIV if such is desirable, or some other suitable enzyme such as peroxidase.

The enzyme-catalyzed deoxygenation systems described herein are operable over a pH range of 6 to 9 with an optimum pH range of 6.5 to 7.5. A temperature range of 0° to 60° C. is suitable with an optimum temperature range of about 40° to 50° C. The enzyme preparations can be stored indefinitely at 0° C. without any appreciable loss of activity. The catalytic enzymes of the subject deoxygenation systems are active over a salinity range of 500 ppm total dissolved solids (TDS) to about 300,000 ppm TDS. In regard to stabilizers, 100 to 500 ppm formaldehyde or about 0.02 weight percent sodium azide is effective in maintaining a high level of enzyme activity in solution within the designated ranges of pH and temperature.

Two exemplary and presently preferred strains of suitable yeasts of the species *Pichia pastoris* have been previously deposited with the United States Department of Agriculture, Agriculture Research Service, Northern Regional Research Laboratories of Peoria, Ill., and have received the numerical designations NRRL Y-11430 and Y-11431.

According to my process, a species of methanol competent Pichia-type yeast is cultured under aerobic aqueous fermentation conditions using methanol as the carbon energy source. Preferably the methanol is supplied under conditions so that methanol is the growth-limiting factor. The methanol-limiting conditions are defined as a concentration of methanol which is the minimum concentration of methanol which results in a maximum growth rate for a given set of fermentation culture conditions. Preferably, the fermentation is conducted under high-cell density conditions, i.e., so that cell density is 50, more preferably 100, grams or greater on a dry weight basis per liter of ferment (cells plus aqueous liquor). The selected yeast is grown in a batch or continuous process in the presence of oxygen, methanol, and an assimilable source of nitrogen. Various types of fermentation processes and apparatuses known in the art can be utilized. For example, a foam-type fermenter such as described in U.S. Pat. No. 3,982,998, or other suitable fermenter can be used.

The needed oxygen can be supplied to the fermenter as such, or in the form of air or oxygen-enriched air, in a range of pressures from such as about 0.1 atm. to 100 atm., as is known in the art.

Fermentation pressures are generally within the range of about 0.1 to 100 atmospheres, more usually about 1 to 30 atmospheres, and more preferably about 1 to 5 atmospheres since the higher pressures result in a higher level of dissolved oxygen in the aqueous medium and usually higher cell productivities.

The assimilable nitrogen source for the fermentation can be any organic or inorganic nitrogen-containing compound which provides nitrogen in a form suitable for metabolic utilization by the microorganisms, such as proteins, amino acids, urea, and the like; and ammonia, ammonium hydroxide, ammonium nitrate, and the like. The presently preferred nitrogen sources include ammonia and ammonium hydroxide for convenience and availability.

The growth of the microorganism is sensitive to the operating temperature of the ferment. Each particular strain of microorganism has an optimum temperature for growth. Exemplary fermentation temperatures are in the range of about 20° C. to about 65° C.

The pH range in the aqueous microbial ferment usually is controlled in the range of about 3 to 7, more preferably and usually about 3.5 to 5.5, by suitable additions of acidic or alkaline materials. Preferences of particular species of microorganisms for a particular pH range are dependent to some extent on the medium employed, as well as on the particular microorganism, and thus may vary somewhat with change in medium as can be readily determined by those skilled in the art.

Sufficient water is maintained in the ferment to provide for the particular requirements of the microorganism employed as well as to provide a carrier fluid for water soluble nutrients. Minerals, growth factors, vitamins, and the like, are added to the element in amounts which vary according to the strain of microorganism utilized and the selected culture conditions, and are known to those skilled in the art or are readily determinable by them. A typical nutrient medium is shown in my examples.

ALCOHOL OXIDASE PREPARATION: ISOLATION

A fluid is prepared which is an aqueous suspension containing cells of the selected microorganism. The aqueous fluid can be fermenter effluent which can be used as is, or preferably after adjusting the pH as described below. Alternatively, the suspended microorganism cells can be initially separated from the fermentation medium, for example, by centrifugation or by filtration through filters having a pore size less than the size of the individual cells, and subsequently resuspended in a convenient volume of water or of an appropriate aqueous buffer, for example $KH_2PO_4/Na_2HPO_4$ buffer at 0.2 M. I have found that the cell density in the aqueous suspension must be greater than a minimum crystallization density. Satisfactory results are obtained if the fluid cell density is greater than about 75 grams on a dry weight basis per liter of fluids. If the fermenter effluent is to be used as the fluid, it should be first adjusted to a pH of such as about 7.5 by addition of a base such as ammonium hydroxide, sodium hydroxide, and the like, for most satisfactory results. The pH is not believed to be critical, and the pH of the aqueous suspension need not be adjusted prior to homogenization. It is preferable to adjust the pH broadly in the range of about 6–9 since in this range the enzyme is active and stable.

The cell-containing fluid can be homogenized by suitable means known to the art. For example, fermenter effluent containing yeast cells grown on methanol at a cell density concentration such as 100–120 grams biomass (dry weight)/liter can be adjusted to a pH of about 7.5 and homogenized using a Dynomill ™ Model KDL using a 0.6 liter vessel in a continuous operation at 5° to 30° C. using belt combination #3 and a flow of 20–30 ml/hr. The homogenate solids are separated from the homogenate to produce a crude solution containing my alcohol oxidase as a soluble component. For example, the homogenate solids can be removed by centrifugation to yield a cell-free supernatant. Alternatively, the solids can be removed by filtration through filters having a suitable pore size, followed by pH adjustment, if desired, for optimum activity. If further purification is desired, such as recovery of crystalline alcohol oxidase, the pH can be adjusted to the range of 5.75 to 6.75 preferably to pH 6.5. The crude solution containing the alcohol oxidase has effective enzymatic activity and finds useful applications in that form.

ALCOHOL OXIDASE PREPARATION: CRYSTALLINE ALCOHOL OXIDASE

The crude solution containing the soluble alcohol oxidase can be treated to recover crystalline alcohol oxidase either in more concentrated solid form such as by fractional precipitation with ammonium sulfate, or most desirably and preferably as the potent crystalline form exhibiting highest activity by treatment under dialysis conditions either by conventional dialysis modes or by applying ultra-filtration to increase the rate of recovery.

In dialysis, the crude solution containing the soluble alcohol oxidase is dialyzed against a dialysis medium across a membrane impermeable to alcohol oxidase but permeable to water, buffer, and inorganic molecules. The crude solution is prepared by homogenizing an aqueous fluid having a cell density effective for crystallization of alcohol oxidase as herein described. Satisfactory crystallization has been observed where the effective cell density is about 75 grams (on a dry weight basis) per liter of aqueous fluid. Crystallization occurs at even lower effective cell densities although the amount of crystalline alcohol oxidase recovered is less. Below an empirically determinable minimum cell density (minimum crystallization density), essentially no crystalline alcohol oxidase is recovered.

The type of membrane used is not considered critical and any suitable membrane may be used. For example, commercially available cellulose acetate dialysis tubing can be used to form dialysis bags, or hollow fiber dialysis cells can be used. The alcohol oxidase containing solution is dialyzed against a dialysis medium, for example water or a buffer solution, to achieve a recovery range solution on the enzyme side of the membrane having an ionic strength in a recovery range of between 0.05 M and 0.01 M thereby effecting precipitation of an electrophoretically homogeneous crystalline oxidase.

The dialysis medium can be any medium whereby during dialysis the molar ionic strength of the solution on the enzyme side of the membrane passes through at least a portion of the recovery range. For example, if the crude solution containing alcohol oxidase has a molar ionic strength of 0.2 M, the dialysis medium can be a suitable volume of distilled water. The volume of fluid against which the enzyme is dialyzed is not considered critical so long as the ionic strength on the enzyme side of the membrane passes through at least a portion of the recovery range.

During dialysis, the pH of the alcohol oxidase containing solution should be maintained in the range of about 5.75 to about 6.75 by use of a suitable buffer system. A suitable buffer system comprises, for example, potassium dihydrogen phosphate and disodium hydrogen phosphate. Preferably the pH range is from about 6.0 to 6.5 for recovery of maximum amounts of crystalline alcohol oxidase. As shown in the example below, good crystallization of the alcohol oxidase has been observed within the broad pH range, and the narrow range represents a presently preferred pH range to achieve minimum solubility of the enzyme.

The alcohol oxidase has minimum solubility under these conditions in solutions of about 0.02 M ionic strength at a pH of about 6.0 to 6.25. Consequently, optimum crystallization is achieved by planning the dialysis to obtain these conditions. Good crystallization can be achieved by exhaustive dialysis of the enzyme-containing solution against large volumes of buffers meeting the above conditions. Alternatively, the dialysis system can be designed to achieve optimal crystallization conditions either at equilibrium or at a point in time after the start of dialysis. For example, a crude enzyme solution having an ionic strength of 0.2 M at pH 6.25 can be dialyzed against a nine-fold excess of distilled water (relative to the volume of the crude enzyme solution). At equilibration, the ionic strength of the crude enzyme solution is 0.02 M and crystallization occurs. Such a method has the disadvantage that a relatively long period of time is required for equilibration to occur.

However, if the crude enzyme solution has a molar ionic strength of, for example, 0.05 M, dialysis against a nine-fold excess of distilled water (relative to the volume of the crude enzyme solution) to equilibration results in a solution having 0.005 M ionic strength and crystals formed will tend to redissolve since the equilibrium ionic strength is outside the recovery range. However, the crystals will form after a relatively shorter dialysis time and can be removed and recovered before system equilibration and redissolution occur. This latter method of dialysis presently is preferred because of the decreased time required to recover crystalline alcohol oxidase.

The dialysis can be safely carried out at temperatures in the range of from about 4° C. to 40° C. Sufficient time, generally more than one hour, and preferably 18 hours or more, is needed for crystallization to occur.

At the end of dialysis, the alcohol oxidase is present in the dialysis bag as a crystalline solid. The crystalline alcohol oxidase can be readily separated from the dialysis medium, such as by decanting the liquid in the dialysis bag from the solid crystals. The moist crystals can be further processed as desired for storage. For example, the crystal slurry can be frozen followed by lyophilization to form a dry powder, or can be dissolved in water or more preferably in a phosphate buffer. The alcohol oxidase can be stored frozen without significant loss of enzymatic activity. Stabilizer compounds known to stabilize enzyme solutions against denaturation and loss of enzymatic activity can be added, such as sucrose or glycerol, or 0.02 weight % sodium azide.

It is suitable to store the prepared enzyme at temperatures in the range of about 4° C. to 40° C., preferably about 4° C. to 24° C. and most preferably at about 4° C. Only minimal loss of activity occurs on storage of the enzyme at 4° C. in 0.1 M phosphate buffer at pH 7.5, and with such as about 0.02% sodium azide to inhibit microorganism growth.

In the process of preparing alcohol oxidase from Pichia microorganisms, a crystalline solid is formed during dialysis of the crude enzyme solution and no further purification steps have been found necessary. The crystalline alcohol oxidase is a readily prepared and relatively inexpensive alcohol oxidase available for applications otherwise economically unattractive.

CHARACTERIZATION OF PICHIA ALCOHOL OXIDASE

The alcohol oxidase isolated from Pichia-type microorganisms is typified by the alcohol oxidase isolated from *Pichia pastoris*. The "Pichia"-derived alcohol oxidase is homogeneous as judged by sodium dodecyl sulfate (SDS) gel electrophoresis. The alcohol oxidase enzyme is estimated to comprise 6 or more subunits, of an estimated molecular weight of 72,000 per subunit as estimated by SDS gel electrophoresis and an estimate of the molecular weight of the alcohol oxidase. The enzyme is a flavoprotein having FAD (flavin adenine dinucleotide) as a coenzyme comprising about one FAD moiety per enzyme subunit. The apparent Michaelis constant, Km, for methanol is about 4 mM. Electrophoretic analysis suggests that the molecular weight of the Pichia enzyme is larger than that of an alcohol oxidase isolated from *Candida boidinii*. The Pichia enzyme differs from an alcohol oxidase isolated from *Hansenula polymorpha* in the extent to which it binds sodium azide, and in its ability to form crystals in 0.02 M sodium phosphate at pH 6.5.

Characteristics of a Pichia-derived enzyme have been determined and are shown in Table I. Reactivities toward various substrates are shown normalized with reference to methanol which is set equal to 100%.

TABLE I

| Characteristic | *Pichia pastoris* |
| --- | --- |
| Molecular wt. | 500,000 (est.) |
| Coenzyme | FAD |
| No. of subunits | 6 or more (est.) |
| Optimal Activity | |
| Temperature (°C.) | |
| (broadly) | 35° to 45°+ |
| (optimum) | 45° |
| pH | |
| (broadly) | 6 to 9 |
| (optimum) | 8.0 |
| Km for methanol | |
| (mM) | 4 |
| Inhibitors | HCHO |
| | >30 mM |

The Pichia-derived alcohol oxidase differs from other reported alcohol oxidases in a number of ways. In particular, the alcohol oxidase from *Pichia pastoris* is reactive toward the lower alcohols and formaldehyde, but is not reactive toward acetaldehyde or organic acids.

According to the invention, the alcohol oxidase can be utilized in any available form. Thus, the alcohol oxidase can be added as a whole cell suspension such as AOPI, as a crude homogenate such as AOPII, as a cell-free supernatant fluid such as AOPIII, or as the purified crystalline enzyme such as AOPIV. Although in most uses the alcohol oxidase can be added to the fluid comprising water and free oxygen, it is also a part of my invention that the alcohol oxidase can be immobilized, for example, on a proper substrate and a fluid containing oxygen and a lower alcohol passed over or through the immobilized enzyme. In either manner, of course, a further enzyme such as catalase or peroxidase, can be co-used where desired or necessary.

EXAMPLES

The following examples are provided as exemplary to assist one skilled in the art to an understanding of the invention. Materials employed, ratios, specific techniques, should not be considered limiting but further illustrative and a part of the overall disclosure.

EXAMPLE I

Thickened Aqueous Polyacrylamide Solutions

The catalytic deoxygenation systems of my process function as solution viscosity stabilizers in thickened aqueous media comprising polyacrylamide and reducing agents such as iron pipe, connate water, ferrous iron, hydrosulfide and hydrosulfite in the presence of ambient oxygen. The solution viscosity stabilizing effect, e.g., of the methanol/methanol oxidase systems including catalase, presumably reflects its capacity to catalyze the removal of $O_2$ and by-product $H_2O_2$.

The removal of dissolved oxygen prevents the oxidative degradation of polyacrylamide to lower molecular fragments and thereby exerts a stabilizing effect on solution viscosity. Such stabilized thickened aqueous fluids for use in tertiary oil recovery operations must exhibit relatively constant viscosities over extended time periods since actual field operations frequently last for many months. Protection of the polymeric viscosifiers is important since the viscosifiers frequently are the most expensive component in enhanced oil recovery operations.

The enzymatic-catalyzed deoxygenation system is effective to preserve the desired viscosity property of the injected fluids.

The runs following demonstrate the inventive process.

Individual 100 g aliquots of aqueous polyacrylamide (500 ppm) mixtures were placed in six separate 125 mL Ehrlenmeyer flasks sealed with rubber serum stoppers. The following preparation of solutions was then carried out before viscosities were measured.
(1) Flask No. 1: 0.5 mL of a 2 weight percent sodium hydrosulfite stock solution was added with 1.5 mL fresh water (500 ppm TDS) to give 100 ppm $Na_2S_2O_4$.
(2) Flask No. 2: 0.5 mL of a 2 weight percent sodium hydrosulfite stock solution and 1 mL of 1 weight percent thiourea stock solution were added with 0.5 mL fresh water (500 ppm TDS) to give 100 ppm $Na_2S_2O_4$ and 100 ppm thiourea.
(3) Flask No. 3: 2 mL of fresh water (500 ppm TDS) was added and the mixture was dexogyenated by bubbling $N_2$ through the solution for one hour.
(4) Flask No. 4: 2 mL of 1 weight percent quebracho stock solution was added to give 200 ppm quebracho.
(5) Flask No. 5: 0.1 mL (0.3 Eu/mL) alcohol oxidase (A cell-free supernatant AOPIII of alcohol oxidase prepared from *Pichia pastoris* was used in the working examples.), 0.05 mL methanol and 1.9 mL fresh water (500 ppm TDS) were added to the polymer solution (100 ppm methanol).
(6) Flask No. 6: The polymer solution was used as a control. The initial viscosity of the polymer solution was 39.4 cp at 75° F.

The above mixtures with the exception of the deoxygenated sample in flask No. 3 were swirled oepn to the air at ambient conditions before sealing with rubber serum stoppers and placing in a water bath at 120° F. for a period of 72 hours. The observed viscosities are recorded in Table II.

TABLE II

Viscosities[a] of Polyacrylamide Solutions With Stabilizing Additives

| Flask No. | Run Type | $O_2$ Scavenger | Visc. (Cp) After 72 Hrs. at 120° F. | Visc. (Cp) After 144 Hrs. at 120° F. |
|---|---|---|---|---|
| 1 | Control | $Na_2S_2O_4$ | 1.9 | 1.8 |
| 2 | Control | Thiourea/$Na_2S_2O_4$ | 23.1 | 20.4 |
| 3 | Control | $N_2$[c] | 30.1 | 27.3 |
| 4 | Control | Quebracho | 9.0 | 3.8 |
| 5 | Invention | Alcohol Oxidase/$CH_3OH$ | 27.8 | 27.2 |
| 6 | Control[b] | None | 24.1 | 19.1 |

[a]Viscosities were measured on a Brookfield LVT viscometer with UL adapter at 6 rpm.
[b]The initial viscosity of the polyacrylamide solution was 39.4 cp at 75° F.
[c]$N_2$ was bubbled through the solution.

Referring to Table II, it can be observed that the solution viscosity stabilization effect of the inventive alcohol oxidase system (Flask No. 5) was comparable to that of the nitrogen deoxygenation system (Flask No. 3) and superior, respectively, to the hydrosulfite system (Flask No. 1), the hydrosulfite/thiourea system (Flask No. 2), the quebracho system (Flask No. 4) and the untreated polymer system (Flask No. 6).

Although sodium hydrosulfite (Flask No. 1) is a recognized oxygen scavenger in the art, poor results were obtained under the conditions of the above runs. Apparently, free radical species produced by the interaction of oxygen and hydrosulfite in the presence of polyacrylamide presumably attack the polymer giving rise to chain scission of the polymer to lower molecular weight fragments and the observed decrease in solubtion viscosity. If all the oxygen is scavenged from the water by hydrosulfite before adding the polymer and the resulting polymer solution is protected from further contact with oxygen, e.g., by storage in a sealed glass capillary viscometer, the solution viscosity was observed to be constant over a period of 100 days. In Flask No. 2, the thiourea perhaps functions as a free radical trap which moderates the proposed polymer scission discussed above and thereby more effectively stabilizes the solution viscosity.

The absence of polymer chain scission (Flask No. 5) during the oxygen scavenging reaction of the alcohol oxidase/methanol system is reflected in the relatively constant solution viscosity over the 144 hour test period. Referring to FIG. 1, it is observed that a 500 ppm aqueous polyacrylamide solution (Hercules NH 335 polyacrylamide) treated with 0.6 Eu/mL alcohol oxidase with 500 ppm methanol exhibited a viscosity of about 40 cp at 75° F. over a period of twenty hours whereas the same aqueous polyacrylamide solution under similar reaction conditions containing hydrosulfite exhibited a viscosity decrease to about 10 centipoises over a 20 hour period.

As indicated above, sodium hydrosulfite must be used to remove the oxygen from water prior to introducing polymer and the resulting mixture then must be protected from subsequent contact with oxygen to avoid loss in solution viscosity.

The alcohol oxidase system continues to scavenge oxygen effectively if the polymer solution is recontacted with oxygen. The alcohol oxidase-methanol system preferably also with catalase can be used in combination with the hydrosulfite system if desired to provide viscosity-stabilized aqueous fluids.

Figure 2:
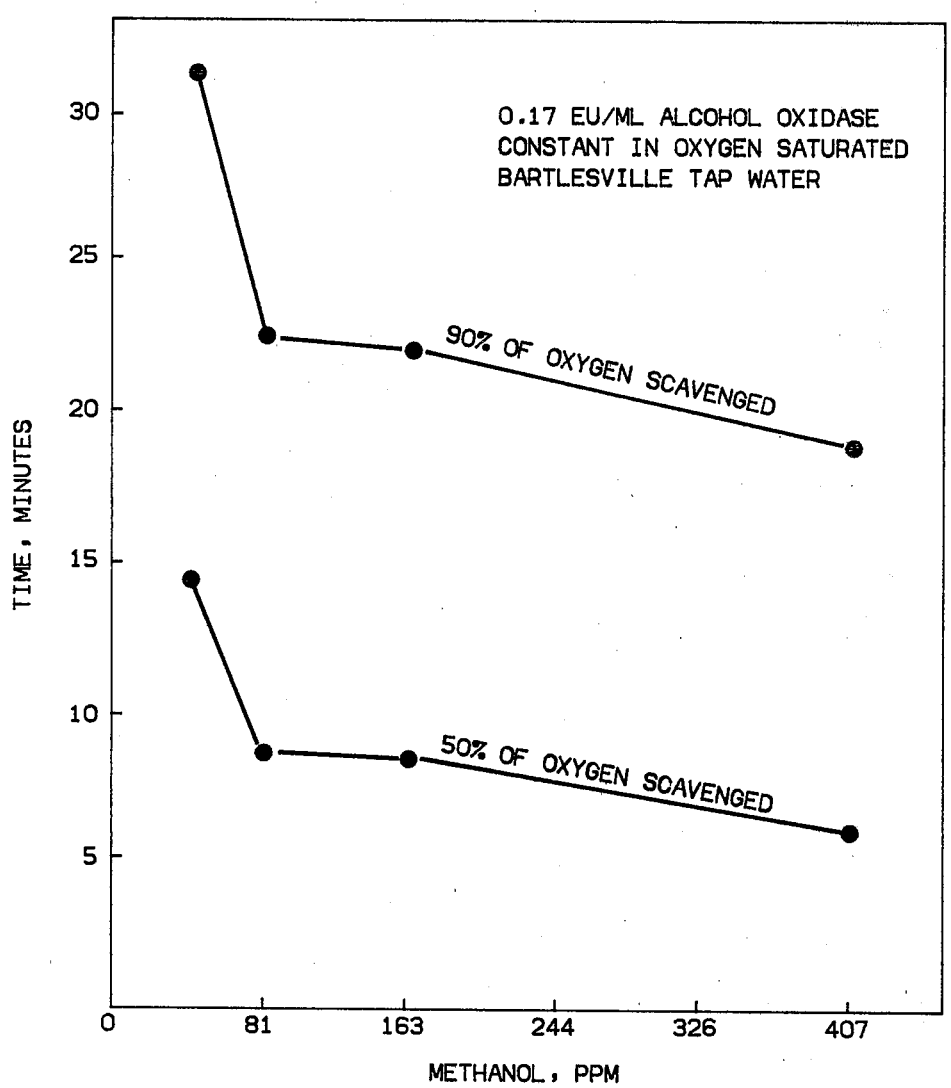
Figure 3:
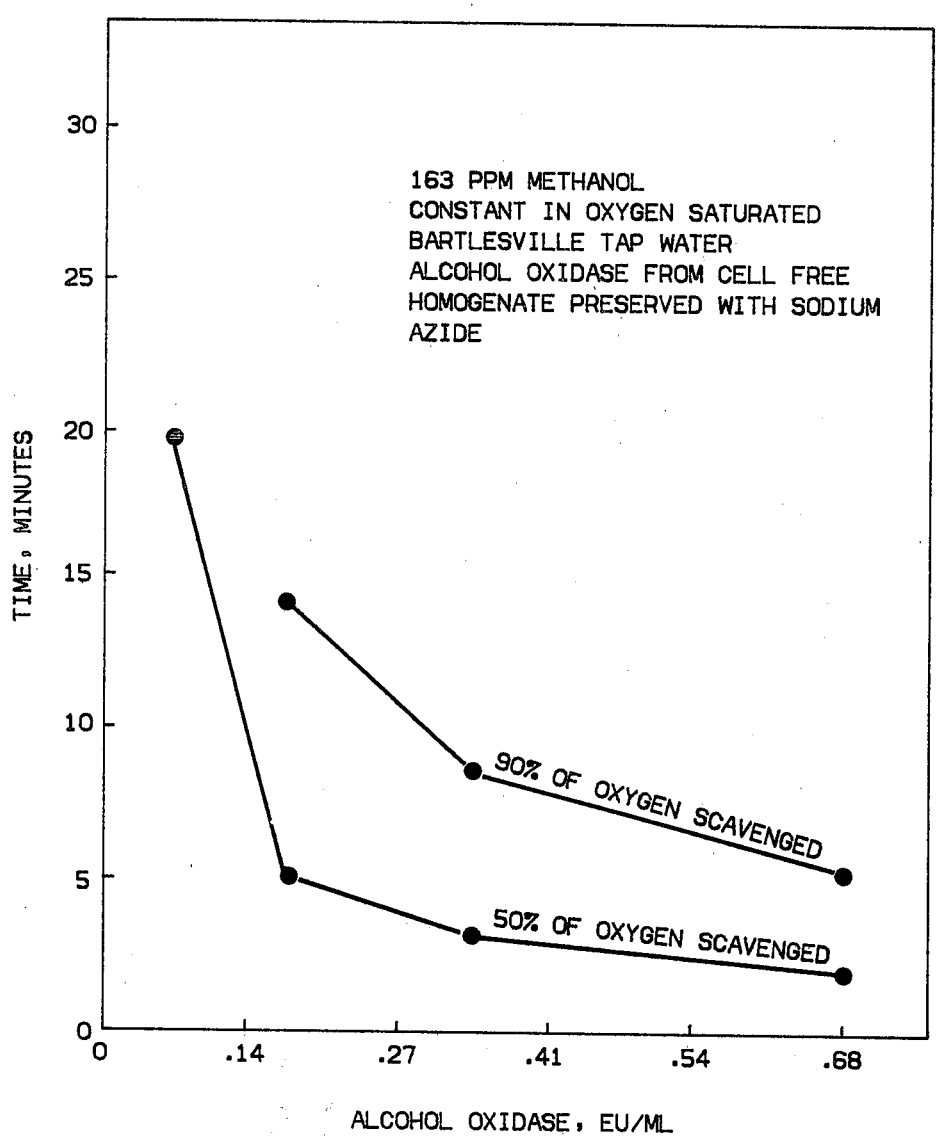

FIGS. 2 and 3 guide the optimum methanol and optimum alcohol oxidase concentrations, respectively, to be used in inventive applications, based on results with oxygen-saturated Bartlesville, Oklahoma, tap water. In FIG. 2, a concentration of 0.17 Eu/mL alcohol oxidase was present in all samples. An enzyme unit (Eu) is that amount of enzyme necessary to convert 1 micromole of methyl alcohol to formaldehyde per minute. As shown in FIG. 2, a concentration of 163 ppm methanol in the system required, respectively, approximately 22 minutes and 9 minutes to remove 90% and 50% of the oxygen present. In FIG. 3, a concentration of 163 ppm methanol was present in all samples. In this system, e.g., it required, respectively, approximately 8.5 and 3 minutes to remove 90% and 50% of the oxygen present with an alcohol oxidase concentration of 0.34 enzyme unit per mL of alcohol oxidase supernatant. On the basis of FIGS. 2 and 3, the optimum concentraton of alcohol oxidase is 0.2 to 0.4 enzyme units per mL of aqueous fluid and the optimum concentration of methanol is about 150 to 200 ppm based on the total fluid volume. Dissolved oxygen concentrations were determined with a Beckman Fieldlab-Oxygen Analyzer. This meter was calibrated with oxygen-saturated water of known composition and temperature.

EXAMPLE II

Alleviation of Oxidative Degradation in Alcoholic Beverages

An undesirable cloudiness develops in bottled beer in the presence of small amounts of oxygen which may be dissolved in the beer and/or be present in small amounts of oxygen which may be dissolved in the beer and/or be present in the space above the top surface of the beer. The combination of an alcohol oxidase-catalase containing deoxygenation system as taught herein can be used to remove ambient oxygen from beer as shown in the example below.

A small sample of bottled beer was allowed to warm to ambient temperature in an open vessel. A 3 mL aliquot of this beer sample was placed in a reservoir and the dissolved oxygen probe (Beckman) was put in place. The oxygen concentration was 100% saturation and was recorded on a strip-chart recorder. At zero time, 1 mL of a crude preparation AOPII of alcohol oxidase containing also catalase (Pichia yeast, 200 Eu/mL) was added, respectively, to beer samples 1 and 2 which has been preadjusted respectively to pH values of 4.15 and 7. The times for the reduction of dissolved oxygen to reach 50% of the initial $O_2$ concentration ($t_{50}$) and 10% of the initial $O_2$ concentration ($t_{10}$) are shown in Table III:

TABLE III

| Sample | pH | $t_{50}$ (Hrs) | $t_{10}$ (Hrs.) |
|---|---|---|---|
| 1 | 4.15 | 2.0 | 6.5 |
| 2 | 7 | 0.1 | 0.5 |

As shown by the results in Table III the alcohol oxidase/catalase containing deoxygenation systems effectively catalyzed the removal of $O_2$ from beer in a reasonably short time.

A similar run showed the deoxygenation effectiveness of the instant alcohol oxidase/catalase system in the presence of 50–60% ethanol which suggests the use of the disclosed catalyst system in hard liquor.

EXAMPLE III

The following run describes the immobilization of alcohol oxidase on substrates such as carboxymethyl cellulose, KELZAN (a commercially available biopolysaccharide viscosifier from Kelco Chemical Co.), activated charcoal optionally in the presence of glutaraldehyde, starch (available, e.g., from Mallinckrodt Chemical Co), and clays such as attapulgite and kaolinite. The alcohol oxidase was a AOPIII homogenate cell-free supernatant originating in a methanol fermentation by a yeast strain of *Pichia pastoris*.

The various support materials were placed in a small evaporating dish and covered with a selected amount of the alcohol oxidase as a homogenate cell-free supernatant (referred to hereinabove as AOPIII). The mixture was hand-stirred and allowed to evaporate at ambient conditions to provide solid residues of the oxidase on the various supports. In order to confirm the enzymatic activity of each residue, 0.1 g portions of each preparation was contacted with a dye-peroxidase assay test solution comprising O-anisidine, water, alcohol and peroxidase. The appearance of a characteristic reddish color in each test indicated that the adsorbed alcohol oxidase was active in catalyzing the removal of dissolved oxygen in the presence of alcohol and water. Representative results are shown in Table IV:

TABLE IV

Alcohol Oxidase On Supports For Catalysis Of Oxygen Removal In The Presence Of Alcohol And Water

| Support (grams) | PHS$^{(d)}$ (mL) | Peroxidase$^{(e)}$- Dianisidine Test | Flow Reactor Test | Remarks |
| --- | --- | --- | --- | --- |
| Carboxymethyl Cellulose (10) | 25 | $(+)^{(f)}$ | NR$^{\#(i)}$ | None |
| KELZAN (10) | 25 | $(+)$ | NR$^{\#}$ | None |
| Starch (10) | 25 | $(+)$ | NR$^{\#}$ | None |
| Attapulgite (5) | (5) | $(\pm)^{**(h)}$ | NR$^{\#}$ | $\neq^{(j)}$ |
| Kaolinite (5) | (5) | $(\pm)^{**}$ | NR$^{\#}$ | $\neq$ |
| charcoal (10) | 15 | $(+)^{(g)}$ | $^{(k)}$ | None |

$^{(d)}$*PHS represents Pichia homogenate supernatant (ca. 280 enzyme units per 25 mL).
$^{(e)}$This test was carried out on the air-dried residues.
$^{(f)}$This activity was still in evidence after a period of eight weeks.
$^{(g)}$The charcoal was soaked in the PHS for 3.5 hours and then contacted for one hour in 20 mL of 2.5% glutaraldehyde in 0.2M phosphate buffer (pH 8). The treated support was then twice washed successively with 1M NaCl in 0.1M phosphate buffer (pH 7.0), 0.005M phosphate buffer (pH 7.0) and water before storing at 4° C.
$^{(h)}$**Indicates that the test results for activity were questionable, however, activity was verified with a "dissolved-oxygen" probe test.
$^{(i)\#}$NR represents that the sample was not run in the flow reactor.
$^{(j)}\neq$ A "dissolved-oxygen" probe test showed alcohol oxidase to be active in these preparations.
$^{(k)}$The treated charcoal support was placed in a glass tubular flow system so that water containing dissolved oxygen and spiked with 0.1 weight percent methanol was passed continuously over the stationary treated support. The effluent was monitored continuously for dissolved oxygen with a dissolved oxygen probe assembly. The water was pumped through the flow system at a rate of 10mL/minute. The dissolved oxygen level in the effluent over a two-day period appeared to stabilize at a level of about 2 ppm. Similar results were obtained with a charcoal preparation which did not involve the use of glutaraldehyde.

The above results indicate that the supported alcohol oxidase samples possess activity to promote removal of dissolved oxygen in the presence of alcohol and water.

The disclosure, including data, has illustrated the value and effectiveness of my invention. The examples, the knowledge and background of the field of the invention and the general principles of chemistry and of other applicable sciences have formed the bases from which the broad descriptions of my invention including the ranges of conditions and the generic groups of operant components have been developed, and formed the bases for my claims here appended.

I claim:

1. The process which comprises treating an aqueous liquid containing dissolved oxygen with sufficient alcohol oxidase and an alcohol, selected from the group consisting of straight-chain alcohols of 1 to 4 carbon atoms, effective to substantially eliminate said dissolved oxygen, wherein said aqueous liquid is an oil field fluid containing a polymer selected from the group consisting of polyacrylamide, carboxyalkyl cellulose ethers, biopolysaccharides and starch, thereby stabilizing said polymer solution.

2. The process of claim 1 wherein said alcohol oxidase is derived from the aqueous aerobic fermentation of methanol-utilizing Pichia yeasts selected from the group consisting of *Pichia pastoris*, *Pichia pinus*, *Pichia trehalophila*, and *Pichia molischiana*.

3. The process according to claims 1 or 2 wherein said alcohol oxidase is employed as:
   (a) a whole single-cell protein suspension further containing catalase;
   (b) a homogenate of ruptured cells further containing catalase;
   (c) a supernatant derived from centrifugation of (a);
   (d) a high purity alcohol oxidase by dialysis of (c); or
   (e) an immobilized form of alcohol oxidase.

4. The process of claim 3 wherein said alcohol oxidase is employed as said (c), (d), or (e), and further employing sufficient added catalase to convert $H_2O_2$ produced by the alcohol oxidase into water.

5. The process of claim 3 wherein said alcohol oxidase is employed as said (c), (d), or (e), and further employing sufficient added peroxidase to convert $H_2O_2$ produced by the alcohol oxidase into water.

6. The process of claim 3 wherein said oil field fluid is a drilling mud.

7. The process of claim 6 wherein said oil field fluid is a brine floodwater.

8. The process of claim 6 wherein said oil field fluid is a surfactant floodwater.

9. A method of stabilizing the viscosity of an aqueous polyacrylamide solution which comprises treating said aqueous polyacrylamide solution with a sufficient amount of alcohol oxidase and an alcohol, selected from the group consisting of straight-chain alcohols of 1 to 4 carbon atoms, effective to substantially eliminate dissolved oxygen in the aqueous polyacrylamide solution.

10. The process according to claim 9 wherein said alcohol oxidase is derived from the aqueous fermentation of methanol-utilizing Pichia yeasts.

11. The process according to claim 10 wherein said alcohol oxidase is employed as:
   (a) a whole single cell protein suspension further containing catalase;
   (b) a homogenate of ruptured cells further containing catalase;
   (c) a supernatant derived from centrifugation of (a);
   (d) a high purity alcohol oxidase by dialysis of (c); or
   (e) an immobilized form of alcohol oxidase.

12. The process of claim 11 wherein said alcohol oxidase is employed as said (c), (d), or (e), and further employing sufficient added catalase to convert $H_2O_2$ produced by the alcohol oxidase into water.

13. The process of claim 11 wherein said alcohol oxidase is employed as said (c), (d), or (e), and further employing sufficient added peroxidase to convert $H_2O_2$ produced by the alcohol oxidase into water.

14. The process which comprises treating an aqueous liquid containing dissolved oxygen with sufficient alcohol oxidase and an alcohol, selected from the group consisting of straight-chain alcohols of 1 to 4 carbon atoms, effective to substantially eliminate said dissolved oxygen, wherein said aqueous liquid is a thickened aqueous polyacrylamide solution and said alcohol oxidase stabilizes the viscosity thereof, and wherein said alcohol oxidase is derived from the aqueous aerobic fermentation of methanol-utilizing Pichia yeasts selected from the group consisting of *Pichia pastoris, Pichia pinus, Pichia trehalophila,* and *Pichia molischiana.*

15. The process according to claim 14 wherein said alcohol oxidase is employed as:

(a) a whole single-cell protein suspension further containing catalase;

(b) a homogenate of ruptured cells further containing catalase;

(c) a supernatant derived from centrifugation of (a);

(d) a high purity alcohol oxidase by dialysis of (c); or (e) an immobilized form of alcohol oxidase.

16. The process of claim 15 wherein said alcohol oxidase is employed as said (c), (d), or (e), and further employing sufficient added catalase to convert $H_2O_2$ produced by the alcohol oxidase into water.

17. The process of claim 15 wherein said alcohol oxidase is employed as said (c), (d), or (e), and further employing sufficient added peroxidase to convert $H_2O_2$ produced by the alcohol oxidase into water.

* * * * *